United States Patent
Finci et al.

(10) Patent No.: US 10,939,854 B2
(45) Date of Patent: Mar. 9, 2021

(54) NONINVASIVE OPTICAL DETERMINATION OF PARTIAL PRESSURE OF CARBON DIOXIDE

(71) Applicant: Radiometer Basel AG, Basel (CH)

(72) Inventors: Julien Finci, Basel (CH); Daniel Salzmann, Yens (CH)

(73) Assignee: Radiometer Basel AG, Basel (CH)

(*) Notice: Subject to any disclaimer, the term of this patent is extended or adjusted under 35 U.S.C. 154(b) by 198 days.

(21) Appl. No.: 15/569,977

(22) PCT Filed: Apr. 18, 2016

(86) PCT No.: PCT/EP2016/058561
§ 371 (c)(1),
(2) Date: Oct. 27, 2017

(87) PCT Pub. No.: WO2016/173877
PCT Pub. Date: Nov. 3, 2016

(65) Prior Publication Data
US 2019/0133504 A1    May 9, 2019

(30) Foreign Application Priority Data
Apr. 30, 2015  (DK) .......................... PA 2015 00260

(51) Int. Cl.
*A61B 5/1455* (2006.01)
*A61B 5/00* (2006.01)

(52) U.S. Cl.
CPC ...... *A61B 5/14552* (2013.01); *A61B 5/14551* (2013.01); *A61B 5/6816* (2013.01); *A61B 5/7214* (2013.01); *A61B 2560/0223* (2013.01)

(58) Field of Classification Search
CPC ....... G01N 21/3504; G01N 2021/0382; G01N 2021/399; G01N 21/05; G01N 21/314;
(Continued)

(56) References Cited

U.S. PATENT DOCUMENTS

| 2008/0231857 A1* | 9/2008 | Depeursinge ...... A61B 5/14552 356/437 |
| 2010/0078563 A1* | 4/2010 | Haveri .................... G01J 3/427 250/339.06 |

FOREIGN PATENT DOCUMENTS

| CN | 101363796 A | 2/2009 |
| CN | 101677766 A | 3/2010 |

(Continued)

OTHER PUBLICATIONS

International Search Report for International Application No. PCT/EP2016/058561, dated Jul. 20, 2016.
(Continued)

*Primary Examiner* — Eric J Messersmith
(74) *Attorney, Agent, or Firm* — Finnegan, Henderson, Farabow, Garrett & Dunner, LLP (57) ABSTRACT

Herein is disclosed a sensor for noninvasive measurement of the partial pressure of CO2 (pCO2) in the skin of a human. The sensor comprises a housing, a gas measuring chamber for measuring gases, at least one chimney for communication of gases diffusing through the skin to the gas measuring chamber, a broad band light source transmitting light into the gas measuring chamber and a detector system comprising a first and a second photodetector. The first photodetector detects light at a wavelength wherein CO2 absorbs light and the second photodetector acts as a zero reference detector by measuring light in a freeband where no gases absorb light.

16 Claims, 6 Drawing Sheets

(58) Field of Classification Search
CPC ............... G01N 21/3518; G01N 21/39; G01N 2201/1215; G01N 2021/3166; A61B 5/1455; A61B 5/14551; A61B 5/6816; A61B 5/14552; A61B 5/7214; A61B 2560/0223
See application file for complete search history.

(56) References Cited

FOREIGN PATENT DOCUMENTS

| | | |
|---|---|---|
| CN | 103975231 A | 8/2014 |
| EP | 1 969 997 A1 | 9/2008 |
| JP | 2010-522868 | 7/2010 |
| JP | 2012-73098 | 4/2012 |
| WO | WO 2004/017054 A1 | 2/2004 |
| WO | WO 2008/110927 A2 | 9/2008 |
| WO | WO 2015/010709 A1 | 1/2015 |

OTHER PUBLICATIONS

Written Opinion of the International Searching Authority for International Application No. PCT/EP2016/058561.

* cited by examiner

NONINVASIVE OPTICAL DETERMINATION OF PARTIAL PRESSURE OF CARBON DIOXIDE

This application is a national stage filing under 35 U.S.C. § 371 of International Application No. PCT/EP2016/058561, filed on Apr. 18, 2016, which claims priority of Danish Patent Application No. PA 2015 00260, filed Apr. 30, 2015. The contents of these applications are each incorporated herein by reference.

TECHNICAL FIELD

Embodiments of the sensor and method disclosed herein relate to the field of non-invasively measuring an analyte concentration in a subject and, in particular, to the measurement of the partial pressure of carbon dioxide ($CO_2$) or other blood gases at a location of a subject's skin, e.g. on an ear lobe.

BACKGROUND

The non-invasive measurement of the partial pressure of blood gases by means of a sensor applied to the skin of a human or animal for measuring the partial pressure of the blood gases has been described in many publications as a useful tool in a number of clinical situations. Sensors for non-invasively measuring blood gases such as carbon dioxide ($CO_2$) and oxygen ($O_2$) are indispensable tools at Intensive Care Units (ICU) and Neonatal Intensive Care Units (NICU) because they provide reliable continuous monitoring of the respiratory function of the patient, human or animal, in a non-invasive way and with minimum amount of work for the hospital staff.

The trend within the field of cutaneous/transcutaneous blood gas sensors is generally to decrease the size of both sensors and monitors. One of the preferred sites for measuring the transcutaneous partial pressure of blood gases is the earlobe, since the skin of the earlobe is very thin. Furthermore, measuring the transcutaneous partial pressure of blood gases is often used on preterm neonates. Irrespective of whether the sensor is used on neonates or on adults it may be difficult to find a suitable flat area on the skin large enough to adequately accommodate a blood gas sensor. Thus the size of the sensor should be minimized.

The sensitivity of the sensor needs to be high since the volume of gases diffusing through the skin is small. They should be able to measure on a small sample volume, and the response time should be short, e.g. no more than 60 seconds. Preferably they should also be calibration and drift free during use.

Commercially available products for cutaneous or transcutaneous measurement of the partial pressure of blood gases are usually electrochemical sensors. These electrochemical sensors have been known for decades to provide an accurate estimate of the partial pressure of blood gases in the skin of the human, from which the arterial partial pressure can be calculated, giving the medical staff at especially ICU, NICU, and sleep laboratories a clear indication of the patients respiratory function, without the need of taking a blood sample. Electrochemical sensors as described are known from e.g. U.S. Pat. No. 6,654,622 B1.

Although electrochemical sensors as known have proven to be indispensable tools at hospitals, they require frequent calibration, the signal may drift, which may cause problems for applications of longer duration, e.g. sleep monitoring, and the require frequent remembraning including adding an electrolyte solution. Hence, it has been a wish to develop another kind of sensor not having these problems.

WO2008110927 discloses an optical sensor using a tunable laser-diode technology, wherein the light beam propagates by single monomodal propagation in a sampling cell, before the light beam is received at a detector, producing an output signal reflecting the chemical substance of the sample.

WO2003023374 discloses an optical sensor using an evanescent field to penetrate into the skin to detect the chemical substance in the skin.

For both of the technologies in WO2003023374 and WO2008110927, the light source is a laser mounted external to the sensor, transmitting light to the sensor via light guides. These systems have several disadvantages as back-light interferes within the laser cavity due to optical interferences on the light pathway, decreasing the sensitivity critically. Furthermore, these systems use a laser light source providing light at one single frequency, which may then be tuned for absorption by one gas, e.g. carbon dioxide, at either the keynote or one of its overtones. However lasers have several disadvantages. Lasers are costly and bulky compared to other light sources. Because of their size lasers were mounted in an external device and the light was transmitted via fiber optics to the sensor. Fiber optics cables are likely to break due to stress after some time of usage. Furthermore, although the laser is tuned to a specific wavelength, the laser drifts due to temperature changes, which has become a problem for the use in sleep monitoring, where the room temperature is lowered overnight, changing the wavelength of the light in the detector system. Hence a system using laser requires constant modulation monitoring to ensure that the laser supplies light at the intended wavelength.

WO2015010709 discloses an optical sensor for detection of $CO_2$ using an Infrared (IR) light source transmitting IR light through an Numerical Aperture (NA) converter and a wavelength filter into a measuring volume having several reflecting surfaces for increasing the signal path, to a detector detecting the amount of light coming through the measuring volume. A change in the light transmitted through the measuring volume is used for estimating the changes in the amount of $CO_2$ in the measuring volume. This is also known in optics as "non-imaging", i.e. the photodetectors are not used for creating an image of the sample in the measuring volume but instead detect changes within the measuring volume.

The term cutaneous in this context means a measurement of the situation in the epidermal layer of the patient, human or animal. The term transcutaneous is often referred to as a measurement wherein the situation beneath the epidermal layer is examined. A transcutaneous measurement is no different from a cutaneous measurement, except that the temperature is higher for transcutaneous measurements whereby the blood flow in the epidermal layer is increased, making the epidermal layer more arterial like, i.e. the epidermal layer behaves more like the layers beneath the epidermis. How much of a temperature increase is necessary to conduct a transcutaneous measurement depends on the skin of the patient. A neonate or preterm neonate has a very thin skin; hence a temperature of e.g. 40° C. may be enough to conduct a transcutaneous measurement of blood gases, whereas elderly people having a thicker skin layer, temperatures of 44° C., or 45° C. may be necessary to arterialize the epidermis. Within the context of this invention it is irrelevant whether the purpose of the measurement is to examine the situation in the epidermis or beneath the epidermis. Hence whether the term cutaneous or transcutaneous is used describing the invention, either term covers that a measurement of the blood gas partial pressure is measured using a sensor applied to the skin of a human.

SUMMARY

The present invention provides in a first aspect a sensor for noninvasive measurement of the partial pressure of CO2 (pCO2) in the skin of a human comprising, a housing, a gas measuring chamber for measuring gases, at least one chimney for communication of gases diffusing through the skin to the gas measuring chamber, a broad band light source transmitting light into the gas measuring chamber, a detector system comprising a first and a second photodetector for detecting light transmitted from the light source through the gas measuring chamber, wherein the first photodetector detects light at a wavelength wherein CO2 absorbs light, characterized in that the second photodetector acts as a zero reference detector by measuring light in a freeband where no gases absorb light.

A sensor according to the invention has several advantages over the prior known sensors. The sensor is calibration free during use, although an initial calibration before leaving the factory is still foreseen. It provides reliable results over long time periods of measuring the $CO_2$ concentration with a short response time. Although the sensor may still have a membrane which may be changed from time to time, the complex remembraning procedure known from the electrochemical sensors is avoided. The sensor is temperature stable, reliable in use and avoids the need of light guides as the light source is a build-in broad band light source, which furthermore is cheaper than a tuneable laser.

A further advantage of the proposed sensor is that it may be designed such that the light is substantially able to travel from the source to the detector in a straight line, without being reflected, which makes the optical system very efficient compared to a system where the light needs to reflect on several surfaces to travel from source to detector. Furthermore, the proposed system provides a measuring chamber where the diffusion of gas into the measuring chamber is perpendicular to the direction of light, which also improves the efficiency since light is less likely to be absorbed by the chimney unintendedly if the incident angle between the light and the chimney is substantially perpendicularly.

In an embodiment of the invention, the second photodetector is optimized for receiving light at a freeband, having a band pass filter centered at 3.9 μm, allowing the sensor to calculate the amount of light absorbed by $CO_2$.

In an embodiment of the invention, the gas measuring chamber has an inner surface of a reflective material such as gold, silver or aluminium, which makes the measuring chamber more reflective and hence a larger amount of light comes through from source to detector.

In an embodiment, the roughness of the inner surface of the measuring chamber is smaller than ¼ λ, providing a smooth surface decreases the risk of back-reflections from the measuring chamber to the source.

In an embodiment the sensor has a beam splitter for dividing the light between the at least two photodetectors, in the form of a reflecting prism or reflective grating, ensuring that the light is received at the photodetector.

In an embodiment the sensor has a measuring chamber with two opposing openings, wherein the first opening is closed by the light source and the second opening is closed by the detector system, hereby providing a straight line between the light source and the detector system and improving the efficient use of the light coming from the source.

In an embodiment the chimneys are perpendicular to the gas measuring chamber, which enhances the efficiency of the gas measuring chamber.

In an embodiment of the sensor, the light source is a light emitting Diode (LED), having a small component size and providing light at a high efficiency.

In an embodiment of the invention, the light source is an infrared light source, which provides the majority of the power in a spectrum where $CO_2$ absorbs the light.

In an embodiment a signal processor is connected to at least one photodetector, for calculation of the difference between the signal at the first and second photodetector and further for calculating the partial pressure of $CO_2$.

In an embodiment the second photodetector is connected to the light source in a feedback-loop, allowing the sensor to auto calibrate the light source such that the light source always provides the same light into the measuring chamber.

In an embodiment of the sensor, the signal processor calculates the partial pressure of $CO_2$ based on the difference between the signal from first and second photodetectors.

In an embodiment of the sensor the total measuring volume has a volume of less than 2 μL, which allows the sensor to have a fast response time.

In an embodiment the sensor is optimized for measuring carbon dioxide, wherein the band pass filter of the second photodetector is centered at 4.26 μm, where $CO_2$ absorbs the light.

In another aspect the invention provides a method for determining the transcutaneous partial pressure of $CO_2$ by irradiating a $CO_2$ gas sample in a gas measuring chamber by a broad band light source, detecting the light transmitted through the gas measuring chamber by a first and a second photodetector, where the first photo detector detects light at a wavelength wherein $CO_2$ absorbs light and the second photodetector detects light at a freeband where no gases absorb light, and calculating by means of a signal processor the $CO_2$ partial pressure based on the difference between the two photo detector signals.

The sensor according to the invention receives gases diffusing through the skin via a number of chimneys that allows the measuring chamber in the sensor to be communicatively connected to the skin of a subject. At one end of the measuring chamber a light source is located emitting light into the measuring chamber. At the opposite end of the measuring chamber a detector system having at least two photodetectors is located. A first photodetector is optimized for receiving light in a spectrum, where light is absorbed by the $CO_2$ to be determined and hereby acts as an active channel. A second photodetector is optimized for receiving light in a spectrum where no gases absorb light, and hereby acts as a zero reference channel. The second photodetector gives a signal showing the total amount of energy transmitted into the measuring chamber. The difference between the signal from the first and second photodetector is used to determine the amount of light absorbed by the $CO_2$ in the measuring chamber, and calculate the partial pressure of $CO_2$.

The light source is a broad spectrum light source e.g. infrared (IR), a light emitting diode (LED), or array of diodes irradiating the measuring chamber with light in a broad spectrum of light covering several wavelengths in the visible or IR range. Depending on the type, and amount of gas within the measuring chamber, different wavelengths will be absorbed by the gas molecules, e.g. $CO_2$ is absorbs light at 4.26 μm. Depending on the quantity of $CO_2$ in the measuring chamber, a percentage of light will be absorbed by the gas molecules, and hence will not reach the photodetector, but be absorbed by $CO_2$ in the measuring chamber. As the light source is a broad spectrum light source, light at many different wavelengths will reach the photodetectors. At 3.9 μm there is no absorption, i.e. 3.9 μm is a freeband, where light is passed from the source to the detector without being absorbed by any gases. A sensor according to the invention will usually be exposed to different gases in two different situations. When the sensor is not in use on the skin of a patient, the sensor is exposed to the gases of free air, i.e. $N_2$ and $O_2$. When the sensor is in use, it is exposed to gases diffusing from the skin of a human patient, i.e. $CO_2$, $O_2$ and water vapor. Hence at 3.9 μm none of these gases interfere the transmission of light from the source to the detector. The light received at the reference channel therefor reflects the amount of light transmitted from the source. The reference channel should be sensitive towards light at 3.9 μm, i.e. a pass band of 3.9 μm±45 nm. Likewise the active photodetector should be sensitive towards e.g. 4.26 μm±90 nm for $CO_2$.

The purpose of the reference channel is to determine the amount of light available without any light being absorbed, to be able to calculate the amount of light absorbed by gas molecules, used for determining the amount of said gas. In an embodiment, the reference channel is also used to adjust the power of the light source. Although the light source is chosen with a very stable performance curve over time and with a breakdown time above the estimated total usage time of the sensor, all light sources degrade over time. Hence the light detected at the reference channel can be used for adjusting the power of said light source, in an auto calibration process.

A light source transmits light in a broad spectrum into the measuring chamber through a window of Ruby or Sapphire that seals the measuring chamber. The light of the spectrum is such that it covers at least both the zero absorption reference channel and the active channel. At the opposite end of the measuring chamber, a lens for rectifying and aligning the light, such as a collimating lens is sealing the measuring chamber. After the lens a beam splitter such as a prism or reflective grating splits the light between the photodetectors. The interrelation of the lens, the beam splitter and the photodetectors is such that the light is split equally between the photodetectors.

The light source may be connected to the reference channel in a feedback loop that allows the input power to the light source to be adjusted to keep the amount of energy supplied from the light source into the measuring chamber substantially at a constant level. In other words, when the properties of the light source changes due to e.g. ageing, the feedback loop adjusts the power supplied to the light source in order to keep the amount of energy supplied into the measuring chamber within a specified range. A feedback loop has the advantage that the sensor may have an auto calibration function, such that no manual calibration is necessary during use of the sensor. If the amount of energy received at the reference channel decreases, the feedback loop may increase the power supplied to the light source to keep the light transmitted into the measuring chamber at a constant level.

The light source may in principle be any type of light source emitting light within the visible or infrared (IR) range. However the light source should of course emit light in a range where light is absorbed by $CO_2$, and in a range where no gases absorb light, to provide for a reference channel. In order to have an effective sensor, that is able to measure small levels of $CO_2$ in the measuring chamber a large amount of photons should enter the measuring chamber, which is why lasers have been preferred in the prior art, since lasers provide large amounts of energy at a specific frequency. For maximum light efficiency the etendue of the detector should act as the limiting aperture. Hence, preferably no light should be lost from the light source through the window, the measuring chamber and the lens. The light source, window, measuring chamber, lens, beam splitter and photodetectors and their interrelation should be chosen such that the etendue of the photodetectors is the limiting factor in the light path from the light source to the photodetectors, to achieve a good signal to noise ratio.

The purpose of the reference channel is to determine the amount of light available when there is no absorption enabling the calculation of the amount of light absorbed by gas molecules, used for determining the amount of said gas. In an embodiment, the reference channel is also used to adjust the power of the light source. Although the light source is chosen with a very stable performance curve over time and with a breakdown time above the estimated total usage time of the sensor, all light sources degrade over time. Hence the light detected at the reference channel can be used for adjusting the power of said light source, as an auto calibration process.

In order to get a high sensitivity in the sensor, the measuring chamber should be optimized so as not to block all light at low levels of partial pressure of the $CO_2$ to be determined, but at the same time absorb a sufficient number of molecules to get a good signal to noise ratio. Table I shows the optimal path length of the measuring chamber for 50 mmHg, and 200 mmHg partial pressure of $CO_2$ and a possible compromise between the two. The optimal path length may be calculated using the Lambert-Beer's Law. Table I further shows the required acceptance angle for the measuring chamber and the maximum inner radius of the measuring chamber, ensuring that light is transmitted from the light source towards the photodetector instead of being reflected backwards towards the light source.

TABLE I

Summary of optimal physical dimensions of the gas measuring chamber

| Parameter: $CO_2$ | Optimization for 50 mmHg | Possible compromise | Optimization for 200 mmHg |
| --- | --- | --- | --- |
| Optical path length | 10 mm | 7 mm | 3 mm |
| Maximum inner radius of Measuring chamber | 0.24 mm | 0.27 mm | 0.44 mm |
| Required acceptance angle of measuring chamber | 44° | 35° | 23° |

In order to keep the response time of the sensor at a reasonable level, e.g. below 2 minutes, the volume should be as small as possible as the amount of blood gases diffusing through the skin of a subject is small. In one embodiment, the measuring chamber, including the chimneys connecting the measuring chamber to the skin of the subject is no more than 2 μL.

The diameter of the measuring chamber can be adjusted to ensure that the total volume of the measuring chamber and the chimneys are no more than 2 μL. As will be understood by the skilled person, the specific configuration of the chimneys and the measuring chamber may be chosen freely, as long as the other requirements such as the optimal path length are taken into account, and that the measuring chamber has a length optimized for the $CO_2$ concentration for which it is intended calculated using e.g. the Lambert-Beer's Law. The proposed design allows sufficient flow between the skin and the measuring chamber that the gas composition in the skin is reflected by the gas composition in the measuring chamber within less than two minutes after the initial warm-up phase, hence the sensor will obtain a result as if it was measuring directly in the skin of the patient.

The measuring chamber may be made by drilling a tube out of a piece of metal such as Aluminum, Gold, Silver, or similar. The finishing of the inside of the measuring chamber should be smooth to enhance the reflectivity. The desired roughness is achieved using suitable tooling and/or polishing. In an embodiment the roughness of the inside of the measuring chamber should be in the range $\frac{1}{4}$-$\frac{1}{20}$ $\lambda$, preferably at least $\frac{1}{8}$ $\lambda$, where $\lambda$ is the middle of the IR spectrum. Alternatively, the gas measuring chamber may be molded in plastic and then spray coated to achieve the desired roughness. Irrespective of the method used to produce the measuring chamber, the reflectivity of the measuring chamber may be increased by coating with any of the previously mentioned materials or with any one of: Wolfram, Molybdenum, Aluminum Oxide, Silicon Nitride, Magnesium Fluoride, Polytetrafluoroethylene, Parylene, or any other suitable material.

The chimneys are perpendicular to the gas measuring chamber and the gas diffusion into the gas measuring chamber is perpendicular to the incident light wave. This has the advantage, that the openings in the gas measuring chamber where the gas enters the gas measuring chamber is less likely to absorb the light or reflect it back towards the light source. Furthermore it makes the likelihood that the light wave collides with $CO_2$ molecules since the forward path of the light and the forward path of the gas diffusion are perpendicular.

To further increase the sensitivity the gas measuring chamber and the prism should have a smooth finishing to ensure a good forward reflection, i.e. ensuring that as much light as possible travels from the light source to the photodetectors. A smooth surface will provide a better signal-to-noise ratio, as a larger percentage of the light will be transmitted from the source to the photodetectors, whereas a rougher surface will give more back-reflection, reducing the amount of light received at the photodetector.

The purpose of the lens is to rectify and collect the light such that it may be split equally between the photodetectors. The light will follow many different paths through the measuring chamber. Some may travel in a straight line from the source to the lens and further to the prism. Others will be reflected several times through the measuring chamber. Hence the lens is used to increase the percentage of light that reaches the beam splitter and is split between the photodetectors, by further rectifying the light.

The beam splitter splits the light between the photodetectors and focuses the light at the aperture of the photodetectors. The beam splitter may be in the form of e.g. a prism or a reflective grating. The prism needs to be aligned optimally, but when aligned is very effective at splitting the light equally, and thus ensuring that a large percentage of the light transmitted into the measuring chamber is received at the photodetectors. The reflective grating is less prone to alignment but is not as efficient as the prism when aligned optimally.

The photodetectors may have a narrow band pass filter with ab steep filter gradient allowing only light in a specific range to be detected, e.g. a center wavelength of 3.9 µm for the zero reference channel, which is a band where no analytes in the gas phase absorb light, and 4.26 µm for detecting $CO_2$. For optimal light efficiency all apertures preceding the photodetectors must be equal to or greater than the etendue of the detector aperture.

One of the photodetectors measures the amount of light received at 4.26 µm, which is the wavelength at which $CO_2$ absorbs light with a filter bandwidth of 180 nm. This detector is also denoted the active channel or the signal detector, since this is the band where $CO_2$ will absorb the light. Detecting a large amount of light with this detector compared to the reference detector means that there is only a small amount, e.g. 0-30% of $CO_2$ in the measuring chamber. The second detector is denoted the reference channel and measures the light at 3.9 µm with a filter bandwidth of 90 nm which is an energy band where no gases absorb light. Subtracting the signals from the two photodetectors gives an indication of the amount of $CO_2$ in the measuring chamber. The output from the photodetectors is a voltage, which is converted into digital signals using A/D conversion. Alternatively some photodetectors provide digital output. The digital signal is used to calculate the partial pressure of $CO_2$ in a calculation unit located in the sensor, or in another device connected to the sensor, by comparing the digital signal with a sensor calibration curve, to determine the amount of $CO_2$ in the gas measuring chamber.

BRIEF DESCRIPTION OF THE DRAWINGS

The above and other aspects will be apparent and elucidated from the embodiments described with reference to the drawing in which.

DETAILED DESCRIPTION

Figure 1:
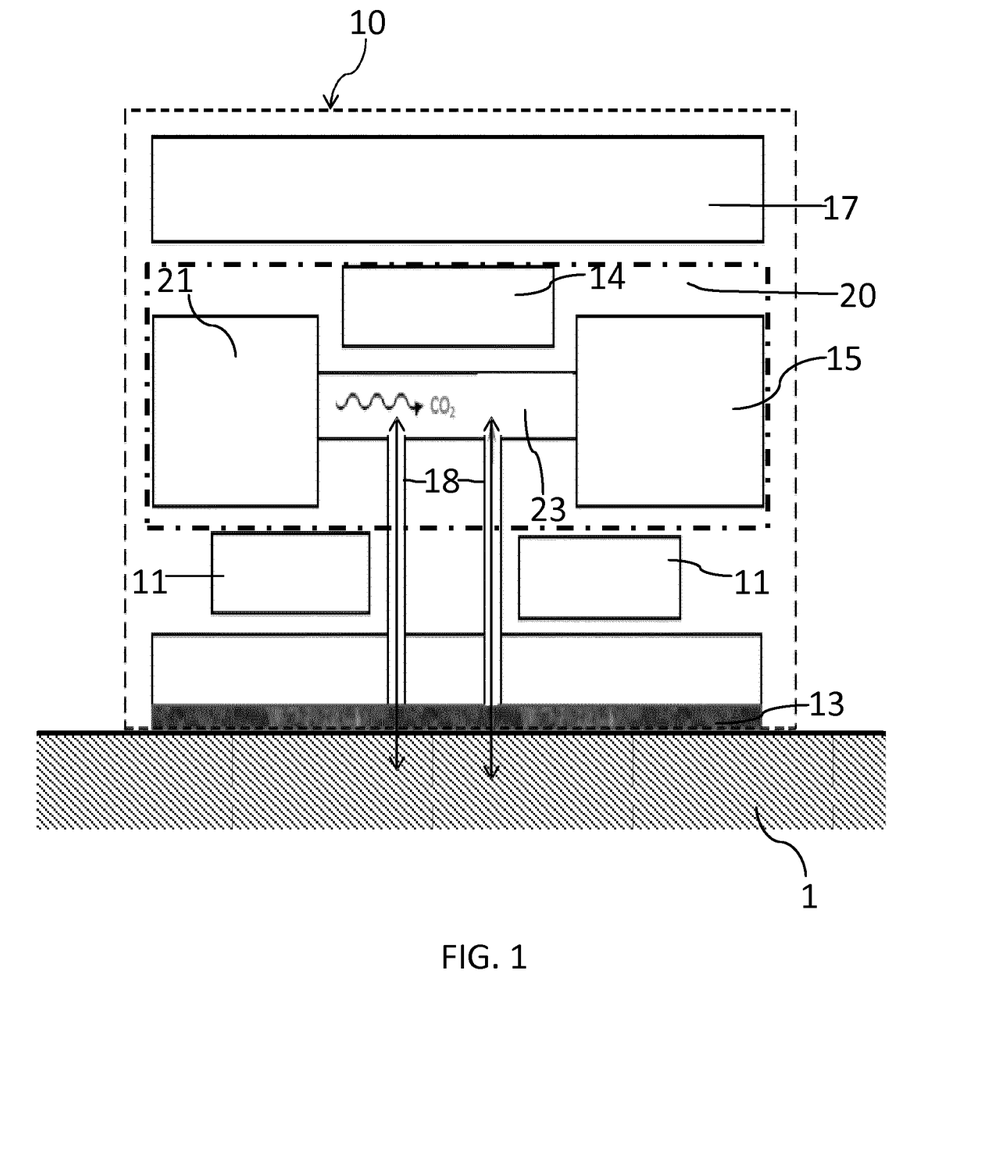
FIG. 1 shows a schematic block diagram of a sensor for measuring the partial pressure of $CO_2$ in the skin of a human patient.

FIG. 1 shows a schematic block diagram of an example of a sensor (10) for measuring the partial pressure of $CO_2$ in the skin (1) of a human patient. The sensor (10) comprises a housing, a measuring unit (20), a patient interface in the form of a membrane (13) contacting the skin (1) of the patient when in use, and protecting the sensor (10) against e.g. moisture and dust. Furthermore, the sensor comprises thermistors (11) for measuring the sensor temperature, used for controlling a heating element (17). The temperature readout from the thermistors (11) is further used for signal processing when converting the detector signal into a partial pressure of $CO_2$ e.g. by the Severinghaus equation. The two chimneys (18) connect a measuring chamber (23) with the skin surface through the membrane (13), whereby gases diffusing through the skin are transported through the membrane (13) and the chimneys (18) to the measuring chamber (23). The measuring chamber (23) is closed off at one end by a light source (21), and at the opposite end by a detector system in the shape of a dual channel detector (15). The skin (1) of the patient, the chimneys (18) and the measuring chamber (23) define a closed system. The electronic board (14) comprises amplification, filtering, A/D converter, and signal processing means. The electronic board (14) communicates with the dual channel detector (15), to convert the signals received from the dual channel detector (15), into a value representing the partial pressure of blood gases in the skin of the patient. Furthermore the signal processing at the electronic board (14) receives information from at least one of the thermistors (11) regarding the sensor (10) surface temperature to control the heating element (17) that heats the sensor (10).

The heating element (17) is used to warm up the sensor (10), which again warms up the skin of the human patient. The thermistors (11) are also used to control the heating element (17), to achieve the correct applied sensor (10) temperature and avoid burning the skin of the patient. The design as described with respect to FIG. 1 has two thermistors (11). One thermistor (11) would be enough for the purpose, but it has become a standard within the industry to have two thermistors (11), doubling the sensor (10) temperature control since it is important to measure the correct temperature for calculating the blood gas partial pressure and to avoid burning the skin of the patient. The heating of the sensor (10) is programmed by the hospital staff, defining measuring time and temperatures. The electronic board (14) also takes care of communication with external equipment (not shown), e.g. a monitor, controller unit connected via electrical cables or smart phones, computers, or tablets connected via wireless means such as WiFi, Bluetooth, GSM or like network.

In an embodiment, the electronic signal processing is performed outside the sensor (10). Hence the electronic board (14) is located in a device, e.g. a monitor external to the sensor (10). Thermistors (11), heating element (17), light source (21), and the dual channel detector (15) is connected to the electronic board (14) in the external device via electrical cabling e.g. in the form of a bus. Preferably A/D and D/A conversion are performed in the sensor (10), such that the communication between the sensor (10) and the external device is digital wired or wireless communication.

The membrane (13) protects the internal parts of the sensor (10), e.g. the electronics, the chimneys (18), and the measuring chamber (23) against intruding particles such as moisture and dust. The membrane (13) is permeable to blood gases, hydrophobic, mechanically robust and does not change the permeability or structural behavior when in contact with alcohol swab, contact gel or sweat. It allows the blood gases to diffuse from the patient skin to penetrate the membrane (13), while blocking dust and moisture from penetrating the membrane (13) to potentially harm the sensor (10), measuring parts, electronics, or block the chimneys (18) and thus obstructing the passageway for the blood gases between the skin of the patient and the measuring chamber (23).

In one embodiment of the invention the chimneys (18) have a diameter of 200 μm and a length of no more than 4 mm. The length of the chimneys (18) should preferably be as short as possible, since the volume of gas within the chimneys (18) adds to the total volume of the gas measuring chamber (23), hence the volume here has negative effect on the sensitivity. Some length is however necessary to allow the photodetector and the light source to be positioned at either side of the measuring chamber (23), and allow the thermistors (11) to be fitted on the surface of the sensor as they need to be close to the skin to detect the skin temperature. The diameter of the chimneys (18) also adds to the total volume and should be chosen as small as possible to in order to keep the response time of the sensor low. On the other hand, larger diameter would decrease the risk of the chimneys (18) being blocked by intruding particles and would also allow a better flow of gas between the skin and the measuring chamber (23). Hence also here a diameter of 200 μm is a compromise. Two chimneys (18) have been chosen since one chimney may increase the risk of partly or fully blocking the chimney, whereas three or more chimneys (18) increase the total volume and the response time. The measuring chamber (23) has a total volume (here including the volume of the two chimneys (18)) of no more than 2 μL, due to the small volume of gas diffusing through the skin per time unit, a large volume would dramatically increase the response time of the sensor (10), which should preferably be no more than one minute. Hence a volume of no more than 2 μL has been found to be a good compromise. The interaction length of the measuring chamber (23), i.e. the length of the measuring chamber (23) wherein the light may interact with the blood gas molecules is in the range of 1.5 mm to 30 mm, see also table I.

Figure 2:
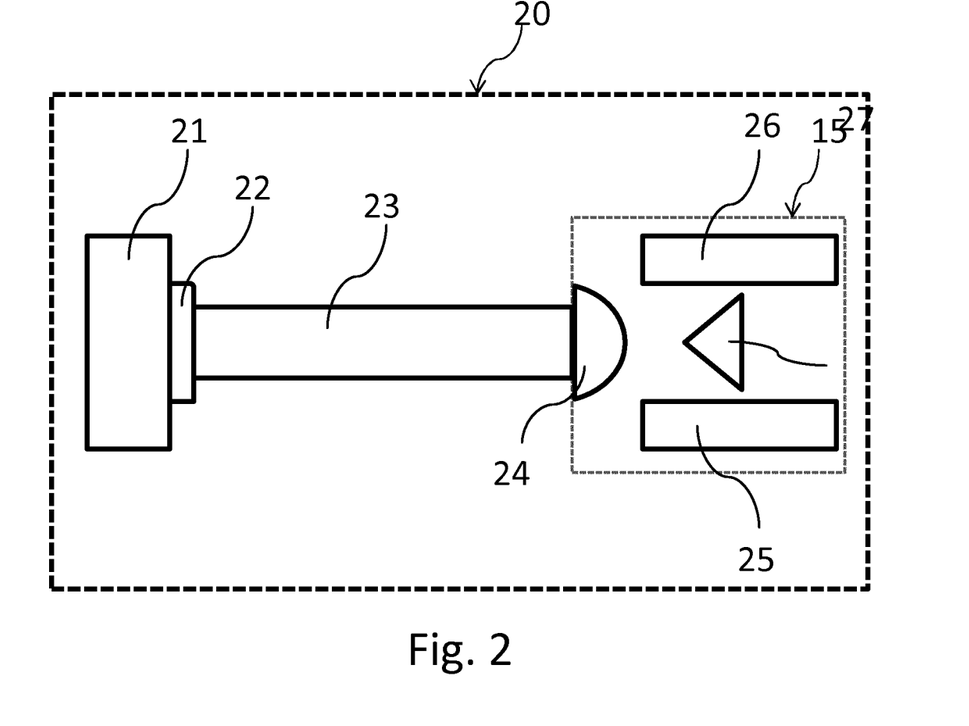
FIG. 2 shows detailed view of the Non Dispersive Infrared (NDIR) detector for measuring partial pressure of $CO_2$.

FIG. 2 is a detailed schematic block diagram of the gas measuring unit (20) comprising the light source (21) transmitting light into the measuring chamber (23) via an IR transparent glass window (22) made of e.g. ruby or sapphire, protecting the light source (21) and sealing the measuring chamber (23), and a collimating lens (24) sealing the opposite end of the measuring chamber (23). The collimating lens (24) is collecting and rectifying the light such that all light are focused at a prism (27). The collecting lens defines the focal point and is chosen such that the prism (27) splits the light equally between two photodetectors (25) and (26). The collimating lens (24), The prism (27), and the two photodetectors (25, 26) together make up the dual channel detector (15). The geometry between the collimating lens (24), the prism (27) and the photodetectors (25, 26) is such that the majority of the light reaching the collimating lens (24) also reach the sensitive point at each of the photodetectors (25, 26) to optimize the sensitivity. The prism (27) is coated with an IR reflective coating, e.g. aluminum, gold, silver, or other suitable material.

To further increase the sensitivity the gas measuring chamber (23) and the prism (27) should have a smooth finishing to ensure a good forward reflection, i.e. ensuring that as much light as possible travels from the light source (21) to the photodetectors (25, 26). Hence the roughness should be ¼ λ to ¹⁄₂₀ λ, at 632.8 nm. A smooth surface will provide a better signal-to-noise ratio, as a larger percentage of the light will be transmitted from the source (21) to the photodetectors (25, 26), whereas a rougher surface will give more back reflection, or scattering, and reduce the percentage of light reflected back towards the source. The gas measuring chamber (23) may be drilled out of a solid piece of metal or another suitable material. The desired roughness is achieved using suitable tooling and/or polishing. Alternatively, the gas measuring chamber (23) may be molded in plastic and then spray coated to achieve the desired reflectivity and roughness.

Figure 3:
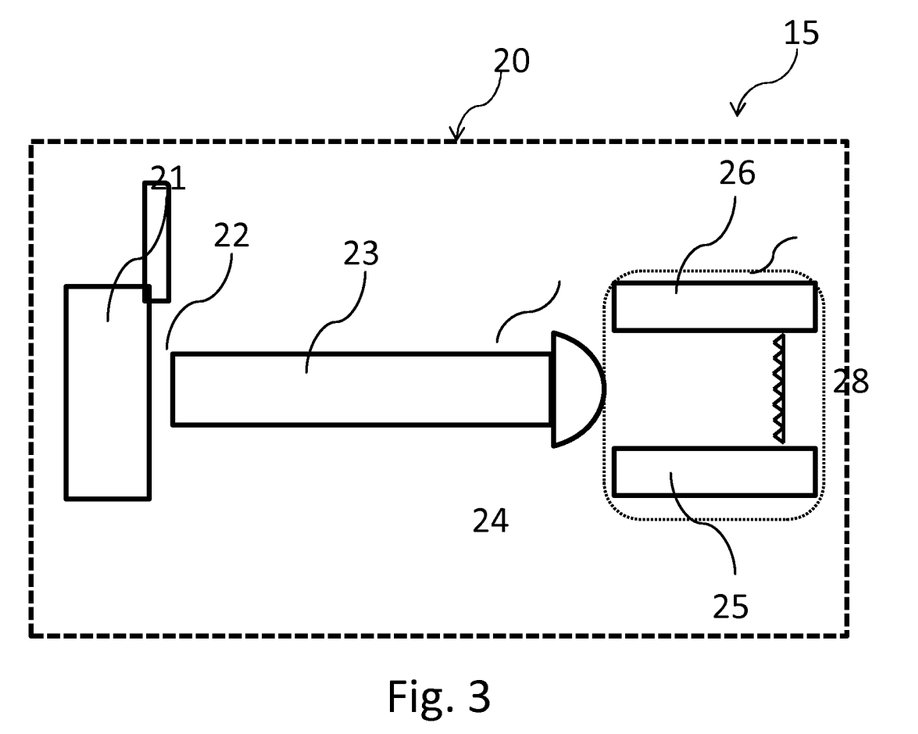
FIG. 3 shows a different embodiment of the NDIR detector for measuring partial pressure of $CO_2$ wherein the prism (27) is replaced with an optical grating (28).

FIG. 3 shows a schematic diagram of an alternative gas sensing unit. The only difference from FIG. 2 is that the prism (27) is replaced with a reflective grating (28) instead of the prism (27). The reflective grating (28) has the advantage compared with the prism (27) that it does not need to be aligned as accurate as the prism (27). However with a correct alignment, the prism (27) is more effective in distributing the light between the two photodetectors (25, 26).

Figure 4A:
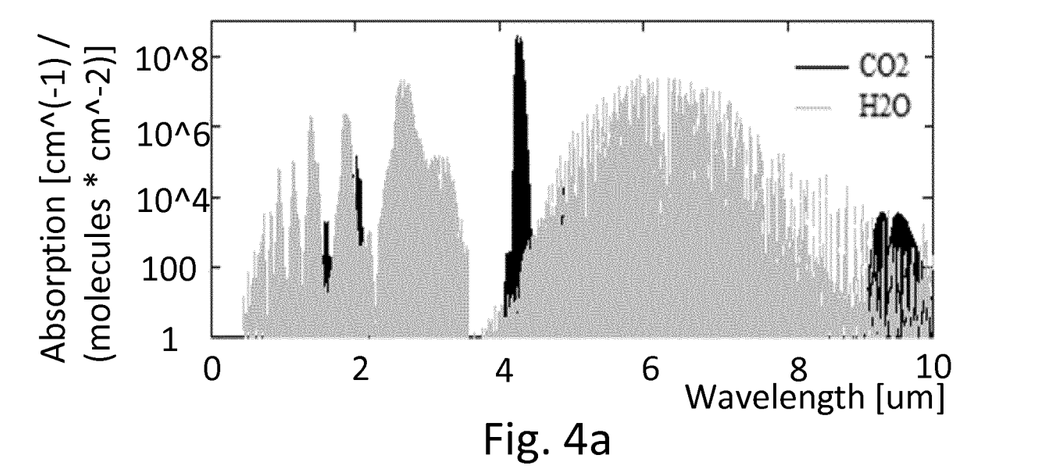
FIG. 4a shows the absorption spectra for water and carbon dioxide in the spectrum 0-10 µm.

FIG. 4a shows the absorption spectra of water and carbon dioxide, in the mid IR spectrum, from 0-10 μm. The spectrum is created using the Hitran database maintained by the Atomic and Molecular Physics Division, Harvard-Smithsonian Center for Astrophysics. Many more gases absorption spectra's are available in the database, but under normal circumstances only water vapour, carbon dioxide, and oxygen diffuses through the skin, and oxygen does not absorb light. Hence it is only relevant to look at $CO_2$ and $H_2O$. As it may be seen, water vapour dominates most of the spectrum, but there are narrow bands where $CO_2$ dominates and also at least one band, where there is essentially no absorbance at all, both are located around the 4 μm wavelength.

Figure 4B:
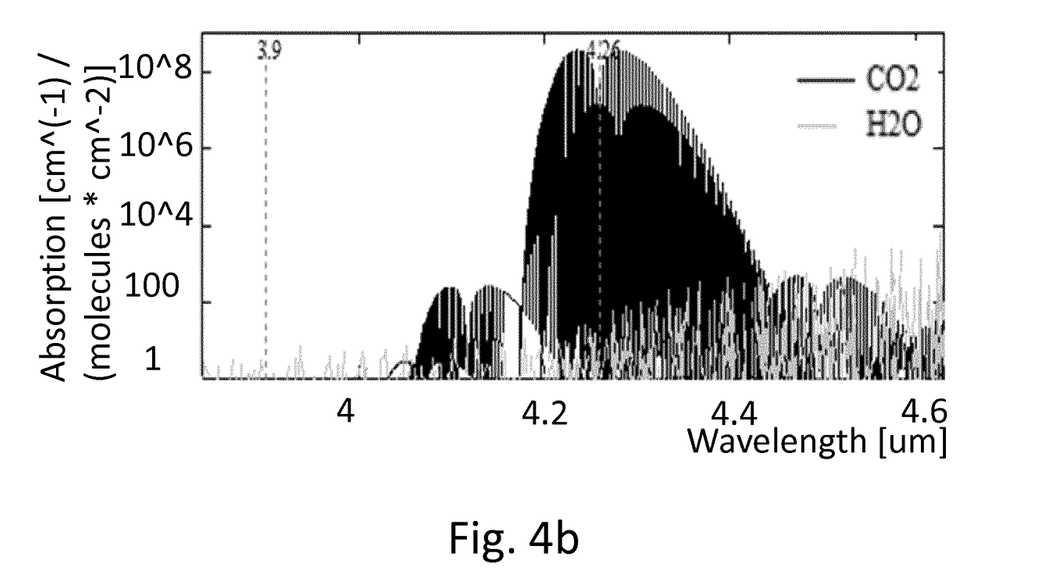
FIG. 4b shows a close-up of the absorption spectra of FIG. 4a focusing on the spectrum of 3.8 µm to 4.6 µm.

FIG. 4b shows a close-up at the spectrum from FIG. 4a around the 4 μm wavelength, where it is already determined that $CO_2$ has a band with great absorption, i.e. around 4.26 μm, and where there is also a free band where essentially no gasses absorb light, i.e. around the 3.9 μm wavelength. This graph may further be used for designing the filters such that they cover a suitable bandwidth and has appropriate steep filter coefficients, such that the photodetector covers exactly the band of interest, e.g. 4.26 μm±90 nm for $CO_2$ and 3.9 μm±45 nm for $O_2$.

Figure 5:
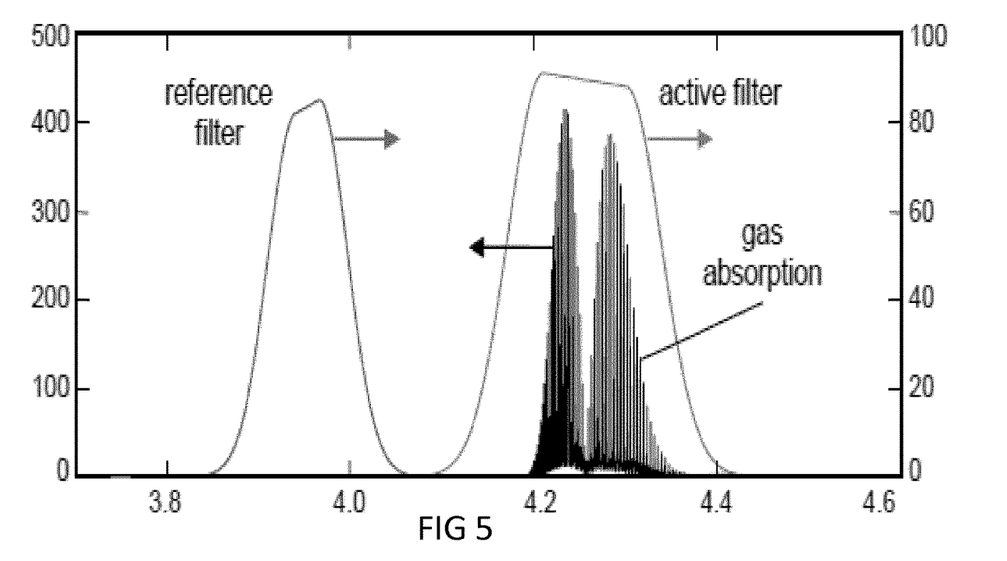
FIG. 5 shows a diagram of the gas absorption spectra for $CO_2$ and the filter function of the active channel and the reference channel, respectively.

FIG. 5 shows the absorption coefficient/cm$^{-1}$ on the left vertical axis and the filter transmission in percentage on the right vertical axis versus the wavelength in μm on the horizontal axis. The spikes show the gas absorption for $CO_2$ and the curved line shows the filter function of the reference channel (left) and the active channel (right). The reference channel is chosen in a freeband where no gas molecules absorb light and hence all light emitted at this wavelength will pass through to the detector and due to the rather steep gradient of the filter function, and the limited band pass filter, of the reference channel detector it will not receive light that is likely to be absorbed by gas molecules. The filter function of the active filter is chosen such that it covers the absorption spectrum for the gas to be determined. The active channel will hence receive light inversely proportional to the amount of gas in the measuring chamber (23). Referring to FIG. 4, it is further seen that there is also a freeband just above the $CO_2$ absorption band where a reference channel could be placed.

Figure 6:
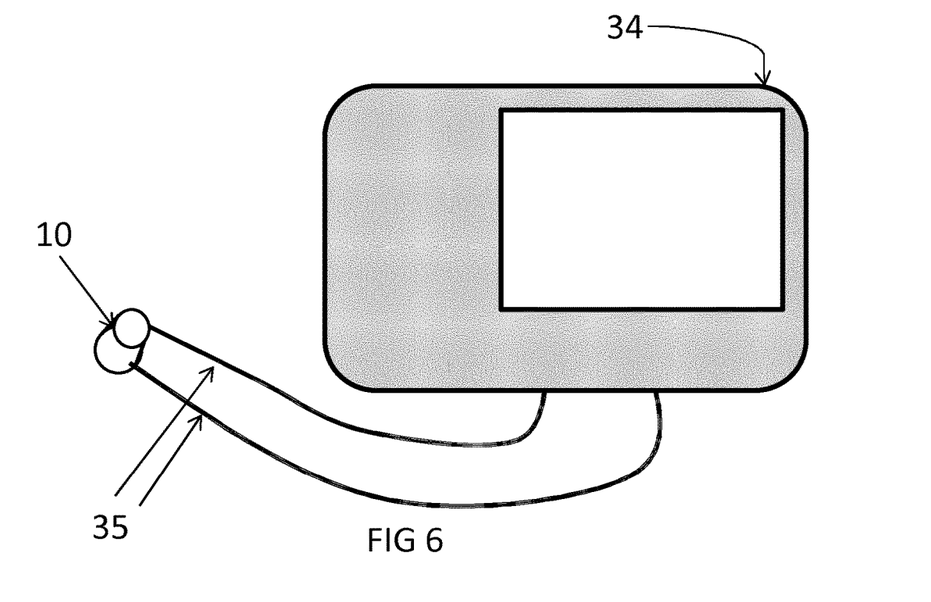
FIG. 6 shows a sensor for transcutaneous measurement of the partial pressure of $CO_2$ in the skin, communicating with a monitor via a wired connection.

FIG. 6 shows a sensor (10) for optically measuring the partial pressure of $CO_2$ in the skin of a patient. The sensor is connected to a monitor device (34) via electrical wires (35). The monitor is further connected to the power grid and hospital information infrastructure (not shown). Although the sensor (10) comprises signal processing means, some of the signal processing may still be conducted by the monitor (34).

Figure 7A:
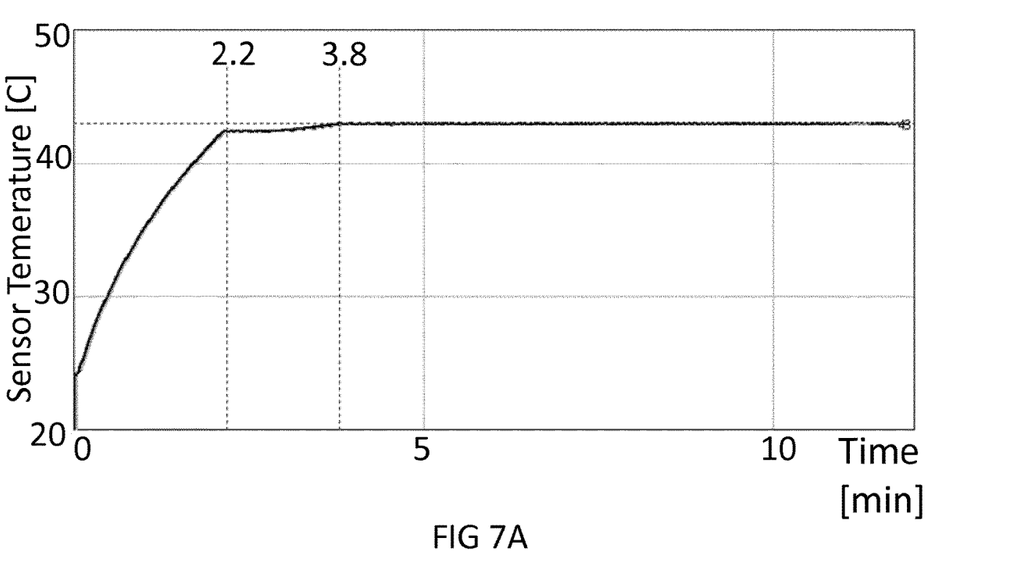
FIG. 7a shows the warm-up time measured for the sensor versus the temperature.

FIG. 7A shows the warm up time for a sensor according to the invention, wherein the sensor temperature [° C.] is plotted as a function of time [minutes]. The temperature is set to 43° C. and the power supplied to the sensor is limited to 500 mW (normally sensors are limited to 1000 mW supply power). After just 3.8 minutes (3 minutes and 48 seconds) the temperature is stable at 43° C. but already after 2.2 minutes (2 minutes and 12 seconds) stable $CO_2$ levels can be determined. Increasing the power limit to 1000 mW, as the todays commercially available sensors, will approximately cut the warm-up time to half the time, i.e. under 120 seconds for reaching a stable temperature of 43° C. and approximately 60 seconds for reaching a stable $CO_2$ level.

Figure 7B:
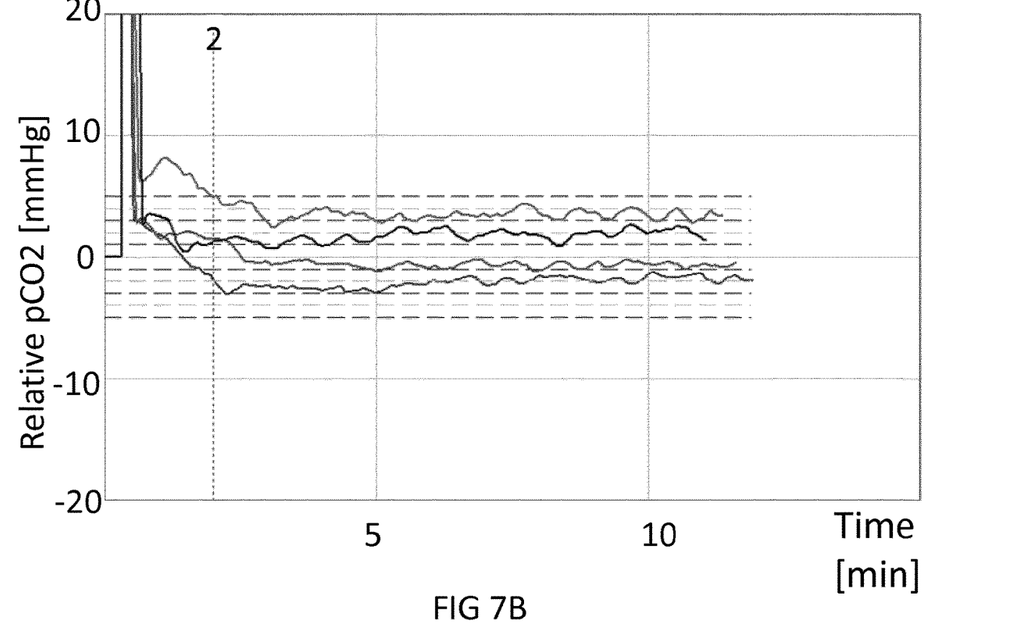
FIG. 7b shows the warm-up time of the sensor versus the relative $PCO_2$[mmHg].

FIG. 7B shows the relative $CO_2$ partial pressure for the warm up time corresponding to FIG. 7A for a test gas with 10% $CO_2$. It can be seen that the $CO_2$ level stabilizes at around 2 minutes from start-up where also the sensor temperature stabilizes. The graph shows 4 different curves with approximately the same course but reaching different levels of $CO_2$. The difference in $CO_2$ level reflects that different light sources have been used giving different sensitivity of the sensor, i.e. the system provides the same stabilization point independent of the light source used. The differences in the levels are handled in the initial calibration process.

EXAMPLE

The sensor (10) as described with reference to FIGS. 1 and 2 is to be placed at the patient's skin (1) for measuring the partial pressure of blood gases in the skin. The membrane (13) is permeable to such gases, whereas moisture, dust etc. is blocked from entering the sensor core. The blood gases travel through the two chimneys (18) and into the measuring chamber (23). The measuring chamber (23), the chimneys (18) and the skin define a closed system. The amount of blood gas molecules in the measuring chamber (23) will thus in time reflect the partial pressure of blood gases in the skin tissue of the patient. At one end of the measuring chamber (23), a light source (21) is located, emitting light into the measuring chamber (23). In the measuring chamber (23) light at 4.26 μm is absorbed by $CO_2$ molecules in the measuring chamber (23) which lead to a weakening of the light intensity at this wavelength, whereas light at 3.9 μm is not absorbed and thus passes through the measuring chamber (23) to be detected by the detector (15). The difference between the light detected with the reference channel (3.9 μm) of the detector and the light detected with the active channel of the detector (4.26 μm) reflects the amount of gas in the measuring chamber (23) and hence the partial pressure of $CO_2$ in the skin tissue of the patient—see FIGS. 2 and 3 for active and reference channel. The difference is calculated by the signal processing device at the electronic board (14). The heating element (17) controls the temperature of the sensor, which in turn controls the temperature of the skin of the patient. Depending on the conditions of the patient it may be necessary to warm up the skin of the patient more in some circumstances than in other. The skin is warmed to temperatures between 25 and 45° C. The temperature is controlled by the feedback system comprising at least one thermistor (11) measuring the sensor surface temperature and feeding back signals to the signal processor at the electronic board (14) controlling the heating element (17).

Tests have been conducted to verify the sensor capability. The tests have been conducted according to Class II special controls guidance document: Cutaneous carbon dioxide ($PcCO_2$) and Oxygen ($PcO_2$) monitors; Guidance for industry and FDA (document issued 2002), and according to ASTM F984.

The sensor was calibrated (initial calibration) by exposing the sensor to gases 1-9, Table II, with a gas flow in the range of 10-20 mL/min in 10 minutes (comprising stabilizing period for each test gas). The last 30 seconds of data is recorded for each gas to establish a median reading. The median values are used as single point for each concentration for the calibration curve. The sensors are further exposed to the gases 1-9 during 10 minutes, before reading the $PCO_2$ values. The last 200 seconds are recorded to evaluate the mean value, the minimum and maximum value and the standard deviation.

TABLE II

Test gases

| Gas | [$CO_2$] | [$O_2$] | [$N_2$] |
|---|---|---|---|
| Test Gas 1 | 0% $CO_2$ | — | Rest $N_2$ |
| Test Gas 2 | 1% $CO_2$ | 90% $O_2$ | Rest $N_2$ |
| Test Gas 3 | 3% $CO_2$ | — | Rest $N_2$ |
| Test Gas 4 | 5% $CO_2$ | 10% $O_2$ | Rest $N_2$ |
| Test Gas 5 | 7% $CO_2$ | 12% $O_2$ | Rest $N_2$ |
| Test Gas 6 | 10% $CO_2$ | — | Rest $N_2$ |
| Test Gas 7 | 15% $CO_2$ | 50% $O_2$ | Rest $N_2$ |
| Test Gas 8 | 20% $CO_2$ | 20.9% $O_2$ | Rest $N_2$ |
| Test Gas 9 | 30% $CO_2$ | — | Rest $N_2$ |

The differences between the calculated values using the gas sensor and the test gas values was determined as can be seen in Table III.

TABLE III

Calculated gas values

| Test Gas | [$CO_2$] % | $pCO_2$ calculated [mmHg] | Min [mmHg] | Max [mmHg] | $pCO_2$ mean measured [mmHg] | Standard deviation 3σ [mmHg] |
|---|---|---|---|---|---|---|
| Test gas 1 | 0 | 0 | 0 | 0.4 | 0.2 | 0.3 |
| Test gas 2 | 1 | 7.4 | 7.8 | 8.3 | 8.1 | 0.3 |
| Test gas 3 | 3 | 22.1 | 21.7 | 22.5 | 22.1 | 0.6 |
| Test gas 4 | 5 | 36.9 | 36.4 | 37.7 | 37.1 | 0.7 |
| Test gas 5 | 7 | 51.6 | 50.9 | 52.2 | 51.5 | 0.9 |
| Test gas 6 | 10 | 73.8 | 73.3 | 75.9 | 74.4 | 1.5 |
| Test gas 7 | 15 | 110.6 | 106.7 | 109.6 | 108.2 | 1.8 |
| Test gas 8 | 20 | 147.5 | 145.9 | 150.5 | 148.4 | 2.8 |
| Test gas 9 | 30 | 221.3 | 214.1 | 221.7 | 218.5 | 4.9 |

The response time of the sensor has been determined according to the class II Special Control Guidance for $tcPCO_2$, ASTM F984 and IEC 60601-3-1. The maximum 10-90% response time is recorded as can be seen from Table IV. The response time was measured at 44° C., the temperature correction factor was set to 1 and the metabolic offset was 0 (zero) mm Hg. The in vivo correction is also 0 (zero) mm Hg. The test procedure was repeated three times. The test was conducted on a sensor as described herein with two chimneys (18) covered by a membrane (13). As can be seen from the 6$^{th}$ column, the acceptance criterion is a response time below 60 seconds. As can be seen the SMD5 component, has a significant longer response time than the rest. The reason for this slow response is that one chimney was blocked, and hence the gases were only able to enter the test measuring chamber (23) via one chimney. Despite the blockade of one chimney (18), the response time is still below the acceptance criteria.

TABLE IV

Response time

| | | 10-90% response time [s] | | | | Test results | |
|---|---|---|---|---|---|---|---|
| Direction | System No. | 1$^{st}$ Cycle | 2$^{nd}$ Cycle | 3$^{rd}$ Cycle | Acceptance Criterion | Passed | Failed |
| Test Gas 3 to Test Gas 6 | SMD1 PI#71 | 41 | 41 | 40 | ≤60 sec for $PCO_2$ | | x |
| | SMD2 PI#72 | 37 | 38 | 36 | | | x |
| | SMD3 PI#73 | 36 | 40 | 34 | | | x |
| | SMD5 PI#74 | 59 | 59 | 54 | | | x |
| Test Gas 6 to Test | SMD1 PI#71 | 44 | 42 | 44 | | | x |
| | SMD2 | 39 | 40 | 41 | | | x |

TABLE IV-continued

Response time

| | | 10-90% response time [s] | | | | Test results | |
|---|---|---|---|---|---|---|---|
| Direction | System No. | 1$^{st}$ Cycle | 2$^{nd}$ Cycle | 3$^{rd}$ Cycle | Acceptance Criterion | Passed | Failed |
| Gas 3 | PI#72 SMD3 PI#73 | 37 | 37 | 39 | | | x |
| | SMD5 PI#74 | 58 | 57 | 56 | | | x |

The invention claimed is:
1. A sensor for noninvasive measurement of the partial pressure of $CO_2$ ($pCO_2$) in the skin of a human comprising:
a housing,
a gas measuring chamber for measuring gases, at least one chimney for communication of gases diffusing through the skin to the gas measuring chamber,
a broad band light source transmitting light into the gas measuring chamber,
and
a detector system comprising a first and a second photodetector for detecting light transmitted from the light source through the gas measuring chamber,
wherein the first photodetector detects light at a wavelength wherein $CO_2$ absorbs light,
wherein the second photodetector acts as a zero reference detector by measuring light in a freeband where no gases absorb light,
wherein the light source is a light emitting diode, and
wherein the second photodetector is connected to the light source in a feedback loop through a signal processor, for auto-calibrating the light source according to the amount of light received at the second photodetector.

2. A sensor according to claim 1, wherein the freeband is centered at 3.9 µm.

3. A sensor according to claim 1, wherein the gas measuring chamber has an inner surface of a reflective material comprising gold, silver, or aluminum forming a reflective tube.

4. A sensor according to claim 3, wherein the roughness of the reflecting tube is less than ¼ of the wavelength of the light absorbed by the gas to be determined.

5. A sensor according to claim 1 further comprising a beam splitter for splitting the light from the collecting lens between the photodetectors of the sensor.

6. A sensor according to claim 1, wherein the measuring chamber has two opposing openings, wherein the first opening is closed by the light source and the second opening is closed by the detector system, thereby providing a straight line between the light source and the detector system.

7. A sensor according to claim 6, wherein the at least one chimney for communication of gases diffusing through the skin to the gas measuring chamber is perpendicular to the gas measuring chamber.

8. A sensor according to claim 1 wherein the light source is an infrared light source.

9. A sensor according to claim 1 wherein the signal processor is connected to the first photodetector and the second photodetector.

10. A sensor according to claim 9, wherein the signal processor calculates the partial pressure of $CO_2$ based on the difference between the signals received at the first and the second photodetector.

11. A sensor according to claim 1, wherein the total volume of the gas measuring chamber and the at least one chimney is no more than 2 µL.

12. A sensor according to claim 1, wherein the first photodetector has a band pass filter centered at 4.26 µm.

13. A method for calculating the partial pressure of $CO_2$ in the skin of a human comprising:
    irradiating a $CO_2$ gas sample in a gas measuring chamber by a broad band light source,
    detecting the light transmitted through the gas measuring chamber by a first and a second photodetector, wherein the first photodetector detects light at a wavelength wherein $CO_2$ absorbs light, and wherein the second photodetector detects light at a freeband where no gases absorb light, and
    calculating by means of a signal processor the $CO_2$ partial pressure based on the difference between the signals received at the first and the second photodetector,
    wherein the light source is a light emitting diode, and
    wherein the second photodetector is connected to the light source in a feedback loop through the signal processor, for auto-calibrating the light source according to the amount of light received at the second photodetector.

14. A sensor according to claim 3, wherein the roughness of the reflecting tube is less than ⅛ of the wavelength of the light absorbed by the gas to be determined.

15. A sensor according to claim 5, wherein the beam splitter is chosen from a reflective prism and a reflective grating.

16. A sensor according to claim 9, wherein the signal processor calculates the partial pressure of $CO_2$ based on the difference between the signals received at the first and the second photodetector.

* * * * *

UNITED STATES PATENT AND TRADEMARK OFFICE
CERTIFICATE OF CORRECTION

PATENT NO. : 10,939,854 B2
APPLICATION NO. : 15/569977
DATED : March 9, 2021
INVENTOR(S) : Julien Finci et al.

Page 1 of 1

It is certified that error appears in the above-identified patent and that said Letters Patent is hereby corrected as shown below:

Claim 13, Column 16, Line 22, "absorb light, and" should read --absorb light,--.

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*